United States Patent [19]

Kordes

[11] Patent Number: Plant 7,479

[45] Date of Patent: Mar. 26, 1991

[54] ROSE PLANT KORENPI

[75] Inventor: Reimer Kordes, Sparrieshoop, Fed. Rep. of Germany

[73] Assignee: Jackson & Perkins Company, Medford, Oreg.

[21] Appl. No.: 308,392

[22] Filed: Feb. 9, 1989

[51] Int. Cl.[5] ..... A01H 5/00

[52] U.S. Cl. ..... Plt./26

[58] Field of Search ..... Plt./18, 26

*Primary Examiner*—James R. Feyrer

*Attorney, Agent, or Firm*—Majestic, Parsons, Siebert & Hsue

[57] ABSTRACT

A rose variety of the Floribunda class is provided having a very long vase life for the buds and flowers, resistance to powdery mildew, and clear pink flowers.

1 Drawing Sheet

SUMMARY OF THE DISCOVERY

The present discovery relates to a new and distinct variety of rose plant of the floribunda class, which I discovered in a cultivated area and I asexually reproduced. This new rose variety is a mutation of the rose plant designated "KORENLO" described and illustrated in U.S. Plant Pat. No. 5,679, inventor Kordes et al issued Mar. 4, 1986, incorporated herein by reference and of common assignment herewith.

The rose plant of the present discovery has a unique combination of characteristics which are outstanding in the new variety and which distinguish it from the rose plant Korenlo as well as from all other varieties of which I am aware. For example, this new rose variety has:

1. Clear pink buds without the characteristic "flame" markings of the Korenlo variety;
2. Clear pink color of the quarter open and full open flower, rather than the mottled Red Group 55A–B of the variety Korenlo; and
3. Efficient production of cut blooms on long, rigid stems.

Asexual reproduction of this new variety by budding, as performed at Wasco, Calif., shows that the foregoing characteristic and distinction comes true to form and is established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose variety, which has been denominated "KORENPI". Color terminology is in accordance with The Royal Horticultural Society Colour Chart except where an ordinary dictionary significance for the color is apparent.

Discovery of this mutation was in a cultivated area (a nursery) and observations of the buds and flowers of the asexually reproduced plant were made in a nursery at Somis, Calif.

Flower

The blooming habit is recurrent and continuous. The bud size is one to one and one-fourth 2 inches when the petals start to unfurl. The bud form is long with a blunt top. By contrast to the Korenlo variety which has a bud color when sepals first divide of mottled Red Group 55A, the bud color when sepals first divide of the new Korenpi variety is near Red Group 52A; when half blown the upper side and the lower side of petals is near Red Group 52B. The sepals have a color near Green Group 138A. There are three appendaged sepals lightly appendaged, and two unappendaged sepals with hairy edge. The receptacle color is near Green Group 138A of a funnel shape, small size and smooth surface. The peduncle is of medium length, nearly smooth surface with a few prickles. Peduncle color is medium green, and the penduncle is stiff and erect.

Bloom

Bloom size is medium, with an average open size of three inches, borne mostly singly. The stems are strong, and long. The form when first open is high center. Al petals curl towards the ends of bloom. Under normal conditions there are 25 to 30 petals. Unlike the Korenlo variety, the upper side of petal at the flower center is near Red Group 52B, as is the reverse side of the petals, and the base of petals has a small white half moon at the point of attachment. The major color is near Red Group 52B. As earlier explained, the Korenlo variety is mottled. The new Korenpi mutation have, however, no variegations. The general tonality at the end of the first day shows no change in color. At the end of the third day, there is slight fading to near Red Group 52C.

There is no fragrance. The petal texture is thick, of a round shape and the edges are slightly quilled.

The arrangement is imbricated with few petaloids in the center. The blooms drop off cleanly, and last both on the plant and as a cut flower for a very long time.

Reproductive Parts

There are many large anthers of yellow color and arranged regularly around the styles. The filaments are light yellow, and the pollen is lemon yellow. The styles are mostly reddish and near white at the base. The stigmas are white.

Plant

A very vigorous, upright growth of bush form.

Foliage

Large size and normal to sparse in quantity. The new foliage is green overlaid with near Grayed-Purple Group 183A, and the old foliage is normal green. Normal mid-stem leaves have five or seven leaflets.

The leaflets are of an elliptic shape, are leathery in texture, and have a serrated edge. The serration is single. Petiole rachis is green with prickles on the underside. Stipules are medium and bearded. The foliage is resistant to mildew under normal growing conditions at Somis, Calif.

Wood

New wood is light green, with a smooth bark. Old wood is green with a smooth bark.

Prickles

There are many to ordinary prickles on main canes from the base and on laterals from the main canes. The form is long and straight. Color when young is brown.

Small Prickles

There are no small prickles on the main stalks or on the laterals.

Parentage

A color mutation of the Korenlo variety.

Classification

Botanical is rosa hybrid. Commercial is Floribunda.

I claim:

1. A new and distinct variety of rose plant of the floribunda class substantially as herein shown and described, characterized particularly as to novelty by the unique combination of good quantity production of long lasting cut blooms of clear pink color, and little fragrance on long rigid stems.

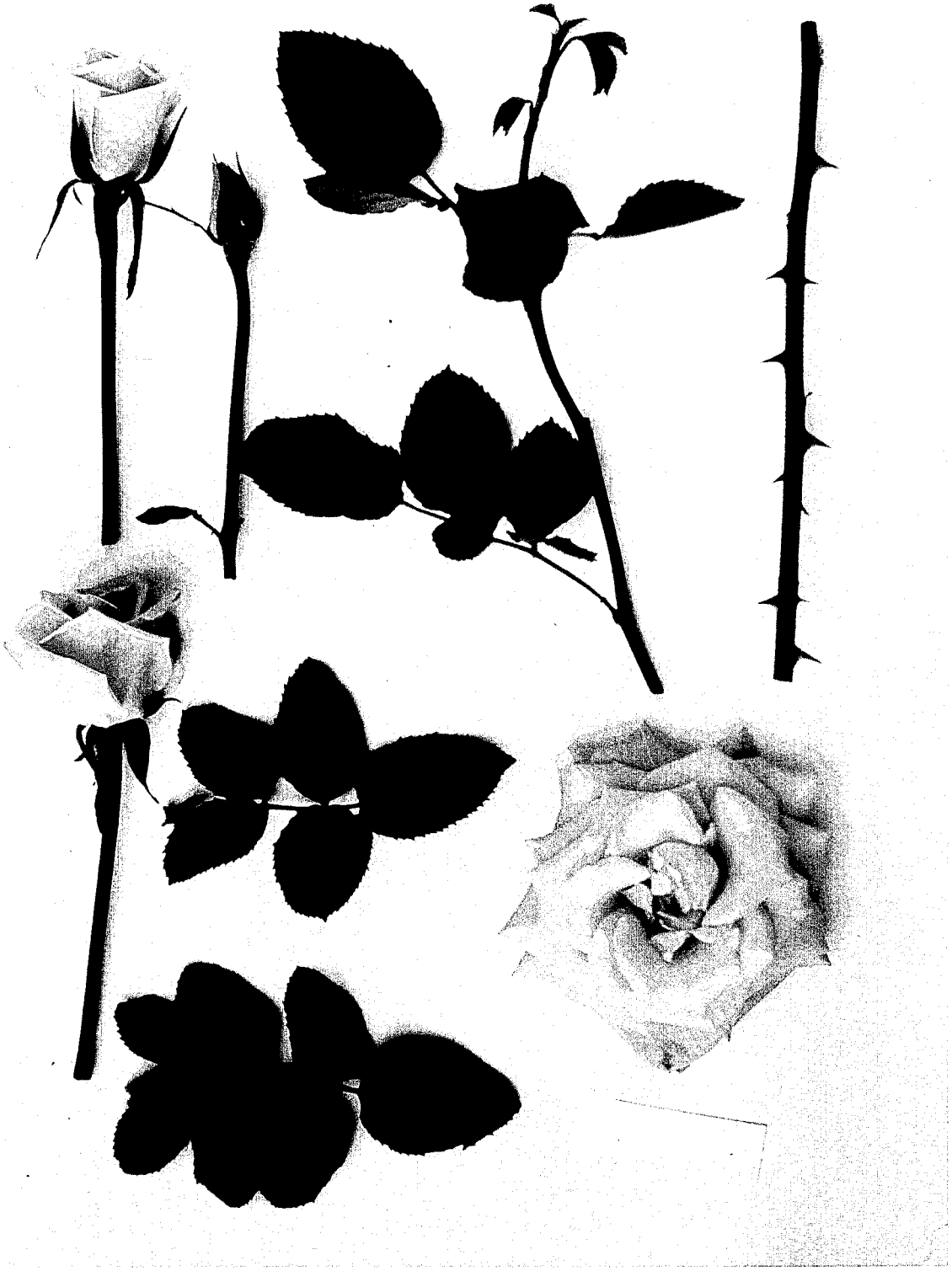

* * * * *